United States Patent [19]

Harrigan

[11] 4,069,913
[45] Jan. 24, 1978

[54] SURGICAL GLOVE PACKAGE AND FIXTURE

[76] Inventor: Roy M. Harrigan, Bromley Mountain Road, Manchester, Vt. 05254

[21] Appl. No.: 603,698

[22] Filed: Aug. 11, 1975

[51] Int. Cl.² .......................................... B65D 85/18
[52] U.S. Cl. ................................ 206/278; 2/161 R; 2/DIG. 7; 128/132 R; 223/111; 206/438; 312/1
[58] Field of Search ............. 206/278, 438, 440, 63.3, 206/69; 2/16, 160, 161 R, 162, 168, DIG. 7; 223/111, 112; 128/132 R, 132 D; 312/1

[56] References Cited

U.S. PATENT DOCUMENTS

| 1,938,685 | 12/1933 | Breuls et al. | 312/1 |
|---|---|---|---|
| 1,996,377 | 4/1935 | Hinchen | 223/111 |
| 2,266,716 | 12/1941 | Robertson | 2/168 |
| 2,299,855 | 10/1942 | Smith | 2/162 |
| 2,641,767 | 6/1953 | La Rosa | 2/168 |
| 2,741,410 | 4/1956 | La Violette | 312/1 |
| 3,018,484 | 1/1962 | Koehn | 128/132 R |
| 3,099,015 | 7/1963 | Renehan | 312/1 |
| 3,140,495 | 7/1964 | Gottwik | 312/1 |
| 3,282,414 | 11/1966 | Penksa | 206/438 |
| 3,337,279 | 8/1967 | Reinhardt et al. | 312/1 |
| 3,476,109 | 11/1969 | Hurney | 206/440 |
| 3,695,493 | 10/1972 | Karr | 312/1 |
| 3,870,150 | 3/1975 | Hummel | 206/438 |
| 4,002,276 | 1/1977 | Poncy et al. | 223/111 |

Primary Examiner—William Price
Assistant Examiner—Bruce H. Bernstein
Attorney, Agent, or Firm—Willis E. Higgins

[57] ABSTRACT

A package for a surgical or similar glove includes a resilient glove having a wrist portion and a hand portion. The wrist portion of the glove is releasably fastened around a glove ring member, with the hand portion of the glove extending from the ring member. An outer, imperforate, flexible member encloses the surgical glove. In a preferred form, the wrist portion of the glove extends through the ring member and is folded over and stretched around the ring member. The outer protective member also extends through the ring member and passes between the stretched wrist portion and the ring member. The outer protective member has a length such that downward movement of the hand after insertion into the glove will cause the glove to push against the bottom of the outer flexible member and thereby cause it to pull the stretched wrist portion of the glove off the ring member.

6 Claims, 5 Drawing Figures

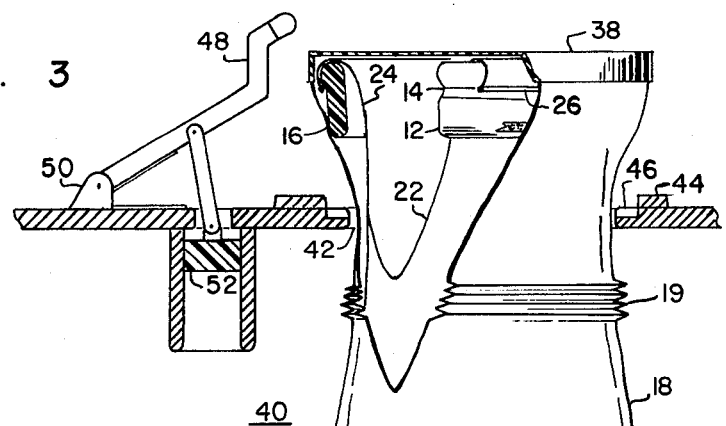
FIG. 3
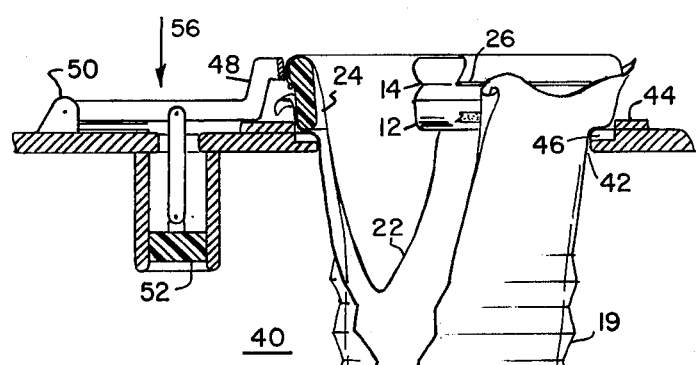
FIG. 5
FIG. 4
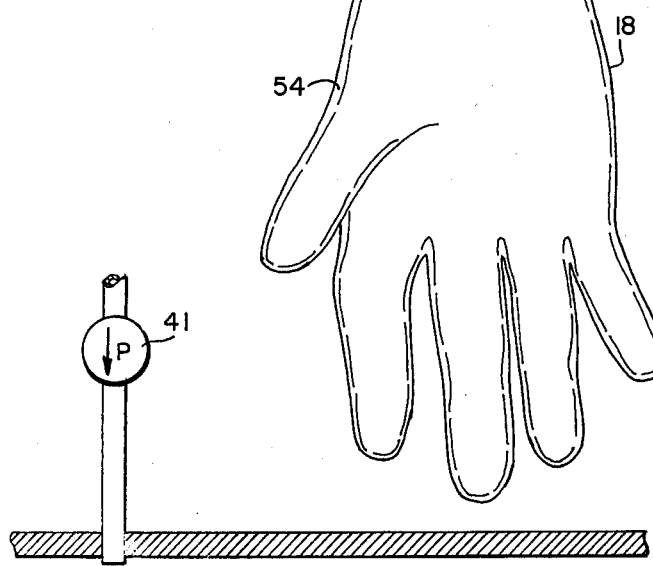

SURGICAL GLOVE PACKAGE AND FIXTURE

FIELD OF THE INVENTION

This invention relates to a package for rubber and flexible plastic gloves, such as surgical gloves. More particularly, it relates to a package for such gloves which facilitates insertion of a wearer's hand into the glove. Most especially, it relates to a package for a surgical glove which facilitates insertion of a wearer's hand into the glove and which serves to protect the glove in a sterilized condition until after completion of the hand insertion.

DESCRIPTION OF THE PRIOR ART

The conventional technique employed for inserting the hand of a wearer into a surgical glove is prone both to damaging the glove and to contaminating it. In the usual procedure, the wrist portion of a surgical glove is held by one person and the wearer thrusts his hand into the glove. This inside of the glove is typically dusted with corn starch, talcum powder or a similar lubricant dust to facilitate insertion of the hand. Should the outer surface of the glove touch a non-sterilized object, it is contaminated and should not be used for surgery. While insertion of a wearer's hand into a surgical glove in preparation for surgery is difficult enough, the situation is compounded when it is necessary to replace a surgical glove during an operation, which is often necessary during surgical procedures. Further, should any of the lubricant powder from the glove enter an open incision it can cause significant post operative problems.

SUMMARY OF THE INVENTION

Accordingly, it is an object of this invention to provide a package construction facilitating the insertion of a wearer's hand into a rubber or resilient plastic glove.

It is another object of the invention to provide a package construction for surgical gloves which facilitates the placement of a wearer's hand into the glove and protects the sterility of the glove until completion of the hand insertion operation.

It is a further object of the invention to provide an improved package for surgical gloves which protects their sterility and is adapted for use with a vacuum apparatus for insertion of a wearer's hand into the glove.

It is still another object of the invention to provide an improved vacuum apparatus for insertion of a wearer's hand into a surgical glove while maintaining sterility of the glove's exterior surface.

The attainment of these and related objects may be achieved through use of the novel glove package and insertion fixture herein disclosed. The package in accordance with the invention comprises a resilient glove having a wrist portion and a hand portion. A glove wrist portion opening member, such as a rigid ring member, is releasably fastened to the wrist portion of the glove, with the hand portion of the glove extending from the wrist portion opening member. The package is used by placing the wrist portion opening member on a support surface having an aperture through which the hand portion of the glove may extend, then inserting the hand into the glove. The glove may be released from the wrist portion opening member by simply pushing down into the glove with the inserted hand with a sufficient extra force to separate the glove from the wrist portion opening member. The hand, now contained in the glove, is withdrawn through the ring or other wrist portion opening member and the glove is ready for use.

For use with a sterilized surgical glove, the package also includes an outer, imperforate, flexible protective member enclosing the surgical glove and also being attached around the ring or other wrist portion opening member, whereby a sealed space is created between the surgical glove and the outer flexible member. The surface of the outer flexible member in contact with the surgical glove is in a sterilized condition. This package structure can be handled in a conventional manner without fear of contaminating the surgical glove, including insertion of the wearer's hand into the glove as described immediately above. If both the outer flexible member and the surgical glove are attached around the ring member by passing the wrist portion of the glove and the end of the flexible member through the ring member, then folding both over the ring member so that the outer flexible member is directly against the exterior of the ring member and the wrist portion of the glove is on top of the end of the outer flexible member, the outer flexible member may be used to release the glove from the ring member. This is done by making the outer flexible member slightly larger than the glove. A wearer's hand may then be inserted into the glove and pushed down a greater extent than required for insertion into the glove so that the glove fingertips push against the outer flexible member a sufficient amount to move its end on the exterior portion of the ring member and slide the overlying wrist portion of the glove off the ring member. With the outer flexible member still attached to the ring member, the now gloved hand may be removed from the package.

As now described, the glove in the package of this invention may have its interior surface dusted with lubricant powder in the conventional manner to facilitate hand insertion. Since the wrist portion of the glove is in sealing relationship with the outer flexible member, none of the lubricant powder can get on the exterior surface of the glove as a contaminant. However, for the reasons discussed above, use of the lubricant powder may be eliminated and the package may be employed with a vacuum chamber having an aperture around which the ring member of the package may be positioned, with the glove and outer flexible member extending inside the vacuum chamber. When a vacuum chamber is to be used for insertion of the wearer's hand into the glove, it is preferred that the configuration of the outer flexible member correspond at least approximately to the shape of the glove in order to prevent over-expansion of portions of the glove. Thus, the outer flexible member can be in the shape of a larger glove or mitten. When the vacuum chamber is evacuated, ambient air pressure causes the outer flexible member and the glove to expand, thus allowing easy insertion of a wearer's hand into the glove. The outer flexible member also serves to protect the sterile outer surface of the glove from contamination by the vacuum apparatus. The outer flexible member may then be used to release the glove from the ring member as discussed above. Alternatively, a means for releasing the glove from the ring member may be included as a part of the vacuum chamber structure.

The attainment of the foregoing and related objects, advantages, and features of the invention should be more readily apparent after review of the following more detailed description of the invention, taken in connection with the drawings, in which:

BRIEF DESCRIPTION OF THE DRAWINGS

FIG. 3 is a perspective view of another embodiment of a package in accordance with the invention with partial cutaways to show detail and showing a cross section portion of a cross section view of a vacuum glove insertion apparatus for use with the package;

FIG. 4 is a side view of a portion of the apparatus in FIG. 3; and

FIG. 5 is another perspective view of the glove package and vacuum glove insertion apparatus of FIG. 3 in use.

DETAILED DESCRIPTION OF THE INVENTION

Figure 1:
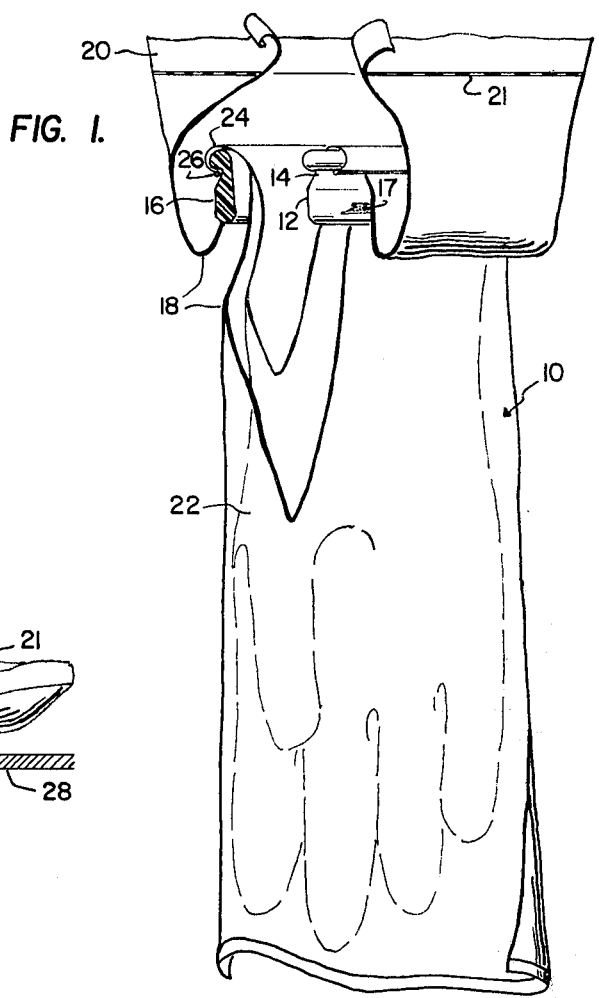
FIG. 1 is a perspective view of a package in accordance with the invention with partial cutaways to show detail.

Turning now to the drawings, more particularly to FIG. 1, basic elements of a glove package 10 in accordance with the invention are shown. A ring member 12, desirably having an oval or round shape to accommodate a person's wrist, is fabricated of a substantially rigid material, such as plastic or metal. The ring member 12 should be able to withstand elevated temperatures employed for sterilization purposes. Ring member 12 has a groove 14 around its outer surface 16. A protective flexible plastic bag 18 extends up through ring member 12 and around its outer surface 16. The protective bag is fastened to the outer surface 16 below groove 14 and 17. Protective bag 18 continues around and up above the ring member 12, where it is heat sealed at 20 to provide a sealed enclosure for sterilized surgical glove 22. To facilitate expansion of glove 22 in a vacuum chamber, air is desirably evacuated from the protective bag 18 prior to sealing if a vacuum chamber is to be used for insertion of a wearer's hand into the glove. A tear strip 21 is provided below the heat seal at 20. The surgical glove 22 extends up through ring member 12 inside protective bag 18. Wrist portion 24 of the surgical glove 22 is folded over ring member 12, with the protective bag 18 between it and the ring member 12. Lip 26 of wrist portion 24 fits at least partially into groove 14.

Figure 2:
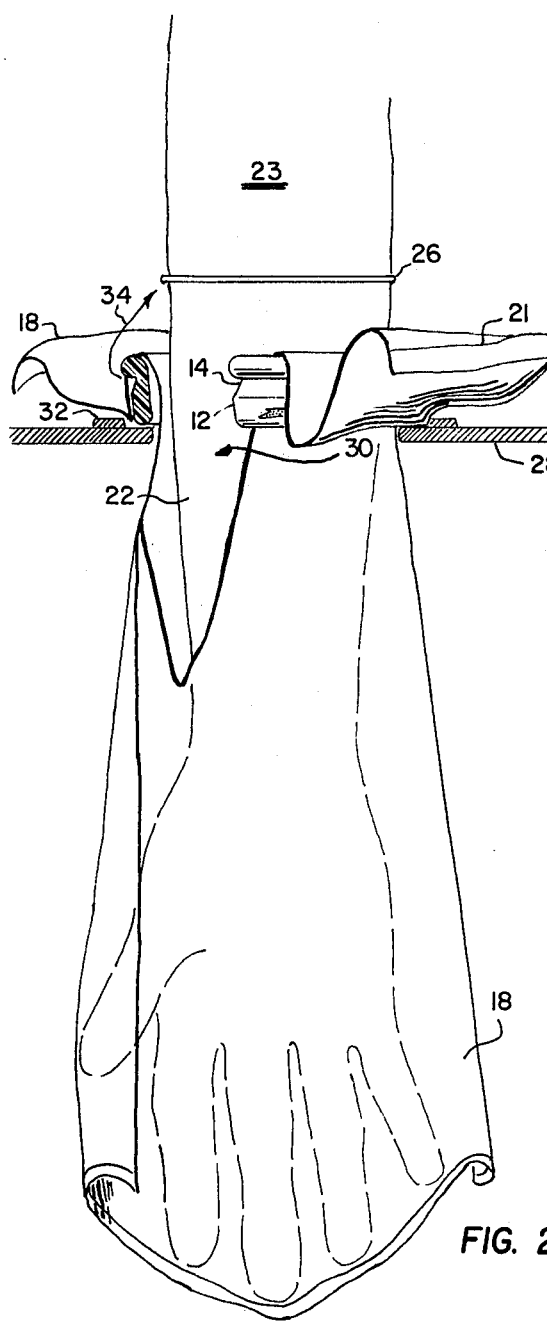
FIG. 2 is a similar perspective view of the embodiment of FIG. 1 in use.

Use of the package in FIG. 1 will now be described with reference to FIG. 2, which shows the surgical glove 22 in place on the hand 23 of a wearer, ready for removal of the glove 22 from its outer protective bag 18. The package of FIG. 1 is placed on a support plate 28 having an aperture 30 large enough to accommodate the hand and wrist of a wearer. Lip 32 around aperture 30 serves to position ring 12 properly with bag 18 and the hand portion of glove 22 extending through aperture 30. The top of outer protective bag 18 is then opened by cutting or tearing, such as along the tear strip 21. Hand 23 is then inserted into glove 22. The glove 22 remains in position on ring member 12 until the fingers of the wearer have been fully inserted in the glove. The wearer then pushes down on the glove, pushing it against outer protective bag 18. Continuing to push down causes outer protective bag 18 to move out of groove 14 on ring member 12, thus pulling lip 26 of glove 22 out of groove 14 on ring member 12 and allowing it to fit around the wrist or lower arm of the wearer, as indicated by arrow 34. Glove 22 is now in place on hand 23, and the gloved hand may now be withdrawn from outer protective bag 18. In this manner, hand 23 is inserted in glove 22, and the glove 22 is disengaged from ring member 12 for easy removal from outer protective bag 18, all without requiring contact of the outer surface of sterile glove 22 by any non sterile member.

FIGS. 3–5 show an alternative embodiment of the invention and its use with a vacuum glove insertion box. Ring member 12, and outer protective bag 18, and a sterilized surgical glove 22, are generally the same as in the embodiment of FIG. 1, except that the outer protective bag 18 now has the shape of a glove of slightly larger dimensions than the inner glove 22 and the hand for which glove 22 is intended. Optional horizontal pleats 19 allow for necessary longitudinal expansion of inner surgical glove 22 during insertion of the wearer's hand. The pleats also serve to hold outer protective bag 18 up in nesting relationship around glove 22 prior to use of the package. If desired, additional horizontal pleats (not shown) could be provided to allow further expansion of the outer protective bag when a vacuum chamber is used for insertion of the glove, thus helping to assure that the glove 22 will expand a sufficient amount for easy hand insertion. Wrist portion 24 of glove 22 extends around ring member 12 with lip 26 in groove 14 as in FIG. 1. However, as can best be seen in FIG. 4, groove 14 does not extend entirely around the periphery of ring member 12. Unlike the embodiment of FIG. 1, glove shaped outer protective bag 18 does not pass through ring member 12, but extends along its outer surface 16. A plastic cap 38 fits over ring member 12, the end of glove 22 and outer protective bag 18 to complete the package.

Vacuum glove insertion chamber 40 constitutes a sealed chamber with the exception of opening 42 through which outer protective bag 18 and glove 22 extend when ring member 12 is positioned inside guide lip 44. In order to seal opening 42 for pulling of the vacuum, a resilient gasket 46 is desirably provided around opening 42. A glove holding member 48 is mounted on vacuum chamber 40 at pivot 50 and has a piston 52 communicating with the vacuum chamber.

FIG. 5 shows glove 22 and outer protective bag 18 expanded in vacuum chamber 40, ready for insertion of a wearer's hand. In operation, a vacuum is pulled in chamber 40 through use of a suitable pump 41. The resulting difference in pressure between the inside of chamber 40 and the outside air causes collapsed outer flexible protective bag 18 to expand. Since outer protective bag 18 and ring member 12 are pushing against gasket 46, expansion of the outer protective bag 18 causes a partial vacuum in the space 54 between it and surgical glove 22. This partial vacuum in turn causes glove 22 to expand, thus allowing ready insertion of a wearer's hand. The vacuum in chamber 40 also causes piston 52 to move downward as indicated by arrow 56, thus pressing glove holding member 48 against lip 26 on glove 22, thus helping to keep the glove in position on ring member 12 until after insertion of the hand.

After the hand has been inserted, pressure in vacuum chamber 40 is returned to normal, thus deflating outer protective bag 18 and, in turn, glove 22 around the hand of the wearer. The return to normal atmospheric pressure also releases glove holding member 48 from engagement with lip 26 of the glove. A slight downward pressure on the glove by the wearer removes lip 26 and wrist portion 24 from ring member 12, first at the portion of ring member 12 around which groove 14 does not extend, then from the remainder of ring member 12.

The wearer's gloved hand may not be removed from protective bag 18 and ring member 12. As in FIG. 2, the wearer's hand may be inserted into glove 22, the glove 22 may be removed from ring member 12, and the gloved hand removed from outer protective bag 18, all without contacting the sterile outer surface of the glove 22.

It should now be apparent that a glove package capable of attaining the stated objects of the invention has been provided. The package, through employing the detachable ring member, facilitates the insertion of a wearer's hand into a rubber or other resilient glove. The package of this invention, whether used with or witout an outer protective bag, can be used either with conventional powdered lubricant for hand insertion or with a vacuum glove insertion chamber.

While the invention has been described with reference to preferred embodiments thereof, it will be readily apparent to those skilled in the art that various changes in form and detail may be made therein. For example, the ring member 12 need not form a closed loop, i.e., it may be C-shaped, with a large enough opening so that a wearer's hand may be moved laterally in the course of separating the glove 22 from the ring member. A ribbon or similar structure could also be used in a manner similar to the outer flexible protective bag 18 in the embodiment of FIGS. 1 and 2 for the purpose of separating the glove 22 from the ring member 12 after insertion of the wearer's hand. Further, a surgical glove and its outer protective member can simply be packaged together in nested relationship, held together by a clip or similar article. The ring or other wrist portion opening member could then be provided as a part of the fixture for using the package. In use of such an embodiment, the nested glove and outer protective member would be fastened over the ring in a manner similar to that shown in FIG. 1. The glove would then be put on a wearer's hand in the same manner as described above. It is intended that such changes be included within the spirit and scope of the claims appended hereto.

What is claimed is:

1. A package comprising:
   a resilient, sterile glove having a wrist portion and a hand portion,
   a ring member which holds the wrist portion of said glove in an open position, releasably fastened to the wrist portion of said glove with the hand portion of said glove extending from said ring member, and
   a flexible protective member completely enclosing and sealed around said resilient glove and being fastened to said ring member so that said resilient glove may be separated from said ring member while maintaining said flexible protective member fastened to said ring member, said flexible protective member having its surface in contact with said sterile glove also in a sterilized condition.

2. The package of claim 1 in which said flexible protective member and the wrist portion of said glove extend through said ring member and are folded over said ring member with the protective member passing between an outer surface of said ring member and the wrist portion, the wrist portion of said glove extending along the outer surface of said ring member a lesser extent than said flexible protective member, whereby a downward force on said flexible protective member will pull the wrist portion of said glove off said ring member.

3. A fixture comprising:
   the package of claim 1 and a support member having an aperture therethrough having a lesser size than said ring member, said ring member resting on said support member, with the hand portion of said glove extending through said aperture.

4. The fixture of claim 3 additionally comprising means on said support member for releasing said glove from said ring member.

5. The fixture of claim 3 in which said support member forms a part of an enclosed chamber sealed by said glove extending through said aperture, said enclosed chamber further having a means of reducing air pressure therein below ambient pressure.

6. A fixture including:
   a sterilized surgical glove having a wrist portion and a hand portion,
   a ring member, the twist portion of said surgical glove being releasably attached around said ring member with the hand portion extending from said ring member,
   an outer, imperforate, flexible member completely enclosing said surgical glove having its surface in contact with said surgical glove in a sterilized condition, having a shape corresponding at least generally to said surgical glove, and being attached around said ring member so that said surgical glove may be separated from said ring member while maintaining said flexible protective member fastened to said ring member, whereby a sealed space is created between said surgical glove and said outer flexible member, and
   a support member for said ring member, said support member having an aperture therethrough having a lesser size than said ring member, with the hand portion of said glove extending through the aperture of said support member.

* * * * *